United States Patent [19]

Orr et al.

[11] Patent Number: 4,879,287

[45] Date of Patent: Nov. 7, 1989

[54] PHARMACEUTICAL COMPOSITION

[75] Inventors: Norman A. Orr; Michael J. Greenway, both of Worthing, England

[73] Assignee: Beecham Group p.l.c., England

[21] Appl. No.: 288,023

[22] Filed: Dec. 21, 1988

Related U.S. Application Data

[63] Continuation-in-part of Ser. No. 940,285, Dec. 11, 1986, abandoned.

[30] Foreign Application Priority Data

Dec. 13, 1985 [GB] United Kingdom ................. 8530796

[51] Int. Cl.$^4$ ............................................. A61K 31/56
[52] U.S. Cl. .................................................... 514/171
[58] Field of Search ......................................... 514/171

[56] References Cited

U.S. PATENT DOCUMENTS

| | | | |
|---|---|---|---|
| 3,178,345 | 4/1965 | Schlagel | 514/171 |
| 4,013,792 | 3/1977 | Eichman et al. | 514/171 |
| 4,082,881 | 4/1978 | Chen et al. | 514/171 X |
| 4,474,751 | 10/1984 | Haslam et al. | 514/171 X |
| 4,524,075 | 6/1985 | Oduro-Yeboah . | |
| 4,604,384 | 8/1986 | Smith et al. | 514/171 X |

FOREIGN PATENT DOCUMENTS

| | | | |
|---|---|---|---|
| 128338 | 12/1984 | European Pat. Off. . | |
| 167856 | 1/1986 | European Pat. Off. . | |
| 851470 | 11/1985 | Greece . | |
| 3756 | 11/1985 | Peru . | |
| 894424 | 4/1962 | United Kingdom | 514/171 |
| 1395907 | 5/1975 | United Kingdom . | |
| 2148116 | 5/1985 | United Kingdom . | |

OTHER PUBLICATIONS

J. Wuite et al., The Lancet, Aug. 13, 1983, p. 394.
Chemical Abstracts, vol. 99, No. 21, Nov. 21, 1983, p. 361, Abstract No. 172689s.
Chemical Abstracts, vol. 104, No. 5, Feb. 3, 1986, p. 20, Abstract No. 28433h.
R. J. Boon et al., Journal of Antimicrobial Chemotherapy, (1985), 16, 519–526.
G. D. Reilly et al., Royal Society of Medicine International Congress and Symposium Series No. 80, edited by D. S. Wilkinson and J. D. Price, The Royal Society of Medicine, London (1984), pp. 73–78.
C. P. Fitzsimons et al., Ibid, pp. 127–129.
L. R. Lever et al., Ibid, pp. 131–136.
C. R. Lovell et al., Ibid, pp. 137–140.
N. B. Simpson et al., Proceedings of an International Symposium, Current Clinical Series 16, edited by R. L. Dobson et al., Excerpta Medica, Elsevier Science Publishers, Amsterdam 1985, pp. 171–176.
J. D. Wilkinson et al., Ibid, pp. 177–182.
C. F. H. Vickers, Round Table Series 4, edited by C. Wood, Royal Society of Medicine Services, Alden Press, Oxford 1986, pp. 32–37.
General Discussion II, Ibid, pp. 38–43.
J. Reid et al., Ibid, pp. 46–49.
General Discussion IV, Ibid, pp. 61–68.
B. I. Davies, Ibid, pp. 69–71.

Primary Examiner—John F. Terapane
Assistant Examiner—Susan Wolffe
Attorney, Agent, or Firm—Jacobs & Jacobs

[57] ABSTRACT

Pharmacuetical compositions for topical application to the skin are disclosed comprising the hydrated crystalline calcium salt of mupirocin and a corticosteriod intimately mixed therewith. The compositions are useful for the treatment of skin disorders in humans and domestic animals.

6 Claims, No Drawings

PHARMACEUTICAL COMPOSITION

The present application is a continuation-in-part application of our copending application Ser. No. 940,285, filed Dec. 11, 1986, now abandoned, which is incorporated herein by reference thereto.

The present invention relates to pharmaceutical compositions of the hydrated crystalline calcium salt of mupirocin for topical application.

Pseudomonic acid, its salts and esters, are known antibiotics and are described in UK patent No. 1,395,907. Topical formulations comprising pseudomonic acid or a salt or ester thereof and polyethylene glycol or polyethylene glycol analogue or derivative are described in European patent publication No. 0 095 897 and European patent publication No. 0 128 338.

The term 'pseudomonic acid' includes all of the four antibacterially active metabolites of *Pseudomonas fluorescens*, i.e. pseudomonic acids A, B, C and D, the structures of which are given by P. J. Baines et al in 'Mupirocin: a novel topical antibiotic', Royal Society of Medicine (London) International Congress and Symposium Series (Editor-in-Chief: H. J. C. J. L'Etang), No. 80 (1984), pages 13-22. The term 'mupirocin' has recently been adopted as the approved name for the major metabolite, pseudomonic acid A, and is used herein to mean pseudomonic acid A.

The present invention provides a pharmaceutical composition for topical application to humans or domestic mammals for treating skin or other disorders, comprising the hydrated crystalline calcium salt of mupirocin and a corticosteroid intimately mixed therewith.

It is an advantageous property of the composition of the present invention that the intimate admixture of the hydrated crystalline calcium salt of mupirocin and a corticosteroid has unexpectedly improved thermal stability as compared to corresponding admixture using the free acid form of mupirocin. The improved thermal stability is unexpected because hydrocortisone has a destabilizing effect on the free acid form of mupirocin and would therefore have been expected to destabilize the hydrated calcium salt as well. The improved thermal stability is a significant advantage because it enables the product to have the required minimum shelf life, even in tropical markets.

It will be understood that the pharmaceutical composition of the invention is prepared by intimately mixing the said components before the composition is applied topically.

It will be further understood that the intimate mixture prepared by the above procedure may include a mixture of the said components in a solid form and/or a solution or suspension of one of the said components in the other said component. The pharmaceutical composition of the invention may comprise a solution and/or a suspension of the said components in a suitable carrier.

Suitably the composition comprises from 0.01 to 50% of the hydrated crystalline calcium salt of mupirocin, preferably from 0.1 to 25%, more preferably from 0.5 to 10%, and especially from 1 to 3%.

All percentages mentioned herein are by weight and based on the total weight of the composition. The percentage of the hydrated crystalline calcium salt of mupirocin given is calculated as the free acid.

Suitably the composition comprises up to 5%, advantageously from 0.001 to 5%, preferably from 0.05 to 3%, more preferably from 0.1 to 2%, of the corticosteroid.

In a preferred aspect of the invention, the composition comprises from 1 to 3% of the hydrated crystalline calcium salt of mupirocin. Suitably the hydrated crystalline calcium salt contains 1.8 to 2.2 moles of water per mole. Normally, the hydrated calcium salt contains from 1.9 to 2.1 moles of water per mole.

Suitable corticosteroids include hydrocortisone, betamethasone, betamethasone valerate, and the like.

Preferably the hydrated crystalline calcium salt of mupirocin and the corticosteroid are incorporated in the formulation in the form of fine particles. Normally such particles will have an average size of less than 50 $\mu$m.

The composition may also comprise additional therapeutic agents such as antimicrobial, antibiotic, antibacterial, antifungal, and antiviral agents, for instance chlortetracycline, miconazole, and idoxuridine, provided that these are compatible with the hydrated crystalline calcium salt of mupirocin. Pseudomonic acid and salts and esters thereof show a tendency to undergo a rearrangement reaction in the presence of acid (that is to say below pH 4) and accordingly acidic agents are unlikely to be compatible with the hydrated crystalline calcium salt of mupirocin. Similarly, pseudomonic acid and salts and esters thereof are not stable in strongly basic media, that is to say above about pH 9.

The compositions of the present invention may be made up in any conventional carriers suitable for the topical administration of antibiotics and corticosteroids, for example paraffins and alcohols. They may be presented, as, for instance, ointments, creams or lotions, eye and ear ointments, gels, impregnated dressings and aerosols. The compositions may also contain appropriate conventional additives, for example preservatives, solvents to assist drug penetration, and emollients.

A particularly suitable composition according to the present invention comprises about 1 to 3% of the hydrated crystalline calcium salt of mupirocin and up to 5% of a corticosteroid. Such a composition may suitably be presented as a cream or ointment for topical application.

A suitable ointment base may conveniently comprise from 65 to 100% (preferably 75 to 96%) of white soft paraffin, from 0 to 15% of liquid paraffin, and from 0 to 7% (preferably 3 to 7%) of lanolin or a derivative of synthetic equivalent thereof.

Another suitable ointment base may conveniently comprise a polyethylene - liquid paraffin matrix, for example that available from Squibb under the trade mark 'Plastibase'.

A suitable cream base may conveniently comprise an emulsifying system, for example from 2 to 10% of polyoxyethylene alcohols (e.g. the mixture available under the trade mark 'Cetomacrogol 1000'), from 10 to 25% of stearyl alcohol, from 20 to 60% of liquid paraffin, and from 10 to 65% of water; together with one or more preservatives, for example from 0.1 to 1% of N,N''-methylenebis[N'-[3-(hydroxymethyl)-2,5-dioxo-4-imidazolidinyl]urea](available under the name 'Imidurea USNF'), from 0.1 to 1% of alkyl 4-hydroxybenzoates (for example the mixture available from Nipa Laboratories under the trade mark 'Nipastat'), from 0.01 to 0.1% of sodium butyl 4-hydroxybenzoate (available from Nipa Laboratories under the trade mark 'Nipabutyl sodium'), and from 0.1 to 2% of phenoxyethanol.

A suitable gel base may conveniently comprise a semi-solid system in which a liquid phase is constrained within a three dimensional polymeric matrix with a high degree of cross-linking. The liquid phase may conveniently comprise water, together with from 0 to 20% of water-miscible additives, for example glycerol, polyethylene glycol, or propylene glycol, and from 0.1 to 10%, preferably from 0.5 to 2%, of a thickening agent, which may be a natural product, for example tragacanth, pectin, carrageen, agar and alginic acid, or a synthetic or semi-synthetic compound, for example methylcellulose and carboxypolymethylene ('carbopol'); together with one or more preservatives, for example from 0.1 to 2% of methyl 4-hydroxybenzoate ('methyl paraben') or phenoxyethanol. ∂Another suitable base may comprise from 70 to 90% of polyethylene glycol (for example, polyethylene glycol ointment containing 40% of polyethylene glycol 3350 and 60% of polyethylene glycol 400, prepared in accordance with the U.S. National Formulary (USNF)), from 5 to 20% of water, from 0.02 to 0.25% of an anti-oxidant (for example butylated hydroxytoluene), and from 0.005 to 0.1% of a chelating agent (for example ethylenediamine tetraacetic acid (EDTA)).

The term 'soft paraffin' as used above encompasses the cream or ointment bases white soft paraffin and yellow soft paraffin. The term 'lanolin' encompasses native wool fat and purified wool fat. Derivatives of lanolin include in particular lanolins which have been chemically modified in order to alter their physical or chemical properties and synthetic equivalents of lanolin include in particular synthetic or semisynthetic compounds and mixtures which are known and used in the pharmaceutical and cosmetic arts as alternatives to lanolin and may, for example, be referred to as 'lanolin substitutes'.

One suitable synthetic equivalent of lanolin that may be used is the material available under the trade mark 'Softisan' known as 'Softisan 649'. Softisan 649, available from Dynamit Nobel Aktiengesellschaft, is a glycerine ester of natural vegetable fatty acids, of isostearic acid and of adipic acid; its properties are discussed by H. Hermsdorf in Fette, Seifen, Anstrichmittel, Issue No. 84, No.3 (1982),p.p. 3-6.

The other substances mentioned hereinabove as constituents of suitable ointment or cream bases and their properties are discussed in standard reference works, for example pharmacopoeia. 'Cetomacrogol 1000' has the formula $CH_3(CH_2)_m(OCH_2CH_2)_nOH$ wherein m may be 15 or 17 and n may be 20 to 24. Butylated hydroxytoluene is 2,6-di-tert-butyl-p-cresol. 'Nipastat' is a mixture of methyl, ethyl, propyl and butyl 4-hydroxybenzoates.

The compositions of the invention may be produced by conventional pharmaceutical techniques. Thus the aforementioned composition, for example, may conveniently be prepared by mixing together at an elevated temperature, preferably 60°–70° C., the soft paraffin, liquid paraffin if present, and lanolin or derivative or synthetic equivalent thereof. The mixture may then be cooled to room temperature, and, after addition of the hydrated crystalline calcium salt of mupirocin, together with the corticosteroid and any other ingredients, stirred to ensure adequate dispersion.

If necessary the composition may be milled at any suitable stage of the process.

A suitable sterilisation procedure may also be included if necessary. Alternatively raw materials are obtained in sterile condition and the compositions are produced aseptically.

The composition of the invention may be applied topically both to the outer skin and to other parts of the human or animal body, for example the eyes and inside the nose. The composition of the invention may also be applied topically to areas in which the skin is missing or damaged, as found, for example, in burns and wounds.

Thus, the present invention further provides a method of treating skin disorders in human or domestic mammals, which method comprises applying topically to a human or domestic mammal in need thereof the composition of the invention.

The invention will now be illustrated by the following Examples:

EXAMPLE 1

Ointment

|  | % w/w |
|---|---|
| Mupirocin, crystalline calcium salt, dihydrate | 2.0 (calculated as mupirocin) |
| Hydrocortisone | 1.0 |
| Ointment base to 100% | |

The ointment base contains:

|  | % w/w |
|---|---|
| White soft paraffin | 95 |
| 'Softisan 649' | 5 |

An ointment formulation was prepared from the above ingredients by the following method. Appropriate proportions of white soft paraffin and 'Softisan 649' were heated together until molten (60°–70° C.) and mixed thoroughly. The mixture was allowed to cool down, with stirring, to room temperature and the hydrocortisone and micronised calcium mupirocin were incorporated using a suitable mixer. The ointment was finally triple-roller-milled.

EXAMPLE 2

Ointment

|  | % w/w |
|---|---|
| Mupirocin, crystalline calcium salt, dihydrate | 2.0 (calculated as mupirocin) |
| Betamethasone valerate | 0.1 (calculated as betamethasone) |
| Ointment base to 100% | |

The ointment base contains:

|  | % w/w |
|---|---|
| White soft paraffin | 95 |
| 'Softisan 649' | 5 |

An ointment formulation was prepared from the above ingredients by the following method.

Appropriate proportions of white soft paraffin and 'Softisan 649' were heated together until molten (60°–70° C.) and mixed thoroughly. The mixture was allowed to cool down, with stirring, to room temperature and the betamethasone valerate and micronised calcium mupirocin were incorporated using a suitable mixer. The ointment was finally triple-roller-milled.

EXAMPLE 3

Ointment

|  | % w/w |
|---|---|
| Mupirocin, crystalline calcium salt, dihydrate | 2.0 (calculated as mupirocin) |
| Hydrocortisone | 1.0 |
| Ointment base to 100% | |

The ointment base contains:

|  | % w/w |
|---|---|
| White soft paraffin | 100 |

An ointment formulation may be prepared from the above ingredients by the following method.

White soft paraffin is heated until molten (60°–70° C.) and the micronised calcium mupirocin and micronised hydrocortisone are incorporated using a suitable mixer. The ointment is then allowed to cool.

EXAMPLE 4

Cream

|  | % w/w |
|---|---|
| Mupirocin, crystalline calcium salt, dihydrate | 2.0 (calculated as mupirocin) |
| Hydrocortisone | 1.0 |
| Cream base to 100% | |

The cream base contains:

|  | % w/w |
|---|---|
| Cetomacrogol 1000 | 3.6 |
| Stearyl alcohol USNF | 14.4 |
| Liquid Paraffin | 42.0 |
| Imidurea USNF | 0.3072 |
| Nipastat | 0.2048 |
| Nipabutyl Sodium | 0.0205 |
| Water to 100% | |

A cream formulation may be prepared from the above ingredients by the following method.

Appropriate proportions of Cetomacrogol 1000, stearyl alcohol and liquid paraffin are heated until molten (60°–70° C.). Micronised calcium mupirocin, micronised hydrocortisone, Nipastat, and Nipabutyl Sodium are added at 60°–70° C. and dispersed. An appropriate quantity of water is then mixed with the oil phase after being heated to a similar temperature. The mixture is homogenised and stirred and allowed to cool to 40° C.. Imidurea is then added and dispersed and the cream is allowed to cool to room temperature.

EXAMPLE 5

Ointment

|  | % w/w |
|---|---|
| Mupirocin, crystalline calcium salt, dihydrate | 2.0 (calculated as mupirocin) |
| Hydrocortisone | 1.0 |
| Ointment base to 100% | |

The ointment base contains:

|  | % w/w |
|---|---|
| Plastibase | 100 |

An ointment formulation may be prepared from the above ingredients by dispersing appropriate proportions of micronised mupirocin, crystalline calcium salt, dihydrate and micronised hydrocortisone in Plastibase at room temperature using a suitable mixture.

EXAMPLE 6

Cream

|  | % w/w |
|---|---|
| Mupirocin, crystalline calcium salt, dihydrate | 2.0 (calculated as mupirocin) |
| Hydrocortisone | 1.0 |
| Cream base to 100% | |

The cream base contains:

|  | % w/w |
|---|---|
| Cetomacrogol 1000 | 3.6 |
| Stearyl alcohol USNF | 14.4 |
| Liquid Paraffin | 42.0 |
| Phenoxyethanol | 1.0 |
| Water to 100% | |

A cream formulation may be prepared from the above ingredients by the following method.

Appropriate proportions of Cetomacrogol 1000, stearyl alcohol and liquid paraffin are heated until molten (60°–70° C.). Micronised calcium mupirocin, micronised hydrocortisone, and phenoxyethanol are added and dispersed. An appropriate quantity of water is then mixed with the oil phase after being heated to a similar temperature. The mixture is homogenised and stirred and allowed to cool to room temperature.

EXAMPLE 7

Gel

|  | % w/w |
|---|---|
| Mupirocin, crystalline calcium salt, dihydrate | 2.0 (calculated as mupirocin) |
| Hydrocortisone | 1.0 |
| Gel base to 100% | |

The gel base contains:

|  | % w/w |
|---|---|
| Water | 98.0 |
| Methylcellulose | 2.0 |

A gel formulation may be prepared from the above ingredients by the following method.

The gel base is prepared by adding the methylcellulose to the water and mixing thoroughly. The micronised calcium mupirocin and micronised hydrocortisone are then added at room temperature and dispersed using a suitable mixer.

EXAMPLE 8

Storage tests were carried out on four formulations designated below as Formulation A, Formulation B, Formulation C and Formulation D.

Formulation A contained the following ingredients:

|  | % w/w |
|---|---|
| Mupirocin, crystalline calcium salt, dihydrate | 2.0 (calculated as mupirocin free acid) |
| Ointment base to 100% | |

Formulation B was the same as Formulation A except that the formulation additionally contained 1% w/w hydrocortisone.

Formulation C contained the following ingredients:

|  | % w/w |
|---|---|
| Mupirocin, free acid | 2.0 |
| Ointment base to 100% | |

Formulation D was the same as Formulation C except that the formulation additionally contained 1% w/w hydrocortisone.

In each formulation the ointment base was identical and contained white soft paraffin (95% w/w) and 'Softisan 649' (5% w/w).

Formulation B is the formulation of Example 1 and was prepared by the method described therein. Formulations A and C were prepared by an analogous method to Formulation B except that the step of adding hydrocortisone was omitted. Formulation D was also prepared by an analogous method to that used to prepare formulation B.

To carry out the storage tests, samples of Formulations A to D were placed in internally lacquered aluminum tubes and kept at a constant temperature (30° or 37°) for 8 months.

Samples were assayed for their mupirocin content after 8 months at 30° C. and after 4 months, 8 months and 24 months at 37° C.. The assay was carried out by high pressure liquid chromatography (h.p.l.c.) analysis using an appropriate standard and the results were expressed as a percentage of the initial mupirocin (that is, mupirocin free acid) content. Except where indicated in the Table below three different samples of each formulation were assayed after each time period (each assay result being the mean of two determinations for each sample) and the mean of the results for the different samples was calculated. The results are shown below.

TABLE

| Storage period and Storage temperature | Formulation A (Ca salt alone) Mupirocin Content (% initial) | Formulation B (Ca salt and hydrocortisone) Mupirocin Content (% initial) | Formulation C (Free acid alone) Mupirocin Content (% initial) | Formulation D (Free acid and hydrocortisone) Mupirocin Content (% initial) |
|---|---|---|---|---|
| 4 months at 37° C. | 101 | 99 | 98* | 93 |
| 8 months at 30° C. | 100 | 100 | 98* | 95* |
| 8 months at 37° C. | 100 | 100 | 72* | 64 |
| 24 months at 37° C. | 98 | 99 | N/A | N/A |

*Mean of assays obtained on two different samples. All other values are the means of three different samples.
N/A - Not assayed - no data available beyond 8 months due to poor stability.

The results indicate:

(a) Formulation A vs. Formulation C

The formulation containing mupirocin free acid as the only active ingredient (Formulation C) was fairly stable when maintained at 30° C. for 8 months or at 37° C. for 4 months. It did, however, show a marked loss of stability when maintained at 37° C. for 8 months and accordingly the test was not continued to 24 months. In contrast, the corresponding formulation containing the crystalline calcium salt dihydrate of mupirocin (Formulation A) was stable under all conditions examined and remained so up to at least 24 months at 37° C..

The above result is not unexpected and is fully in accord with the disclosure in European patent application publication No. 167 856 which it was stated, and demonstrated, that calcium pseudomonate, when isolated in crystalline form, showed good thermal stability relative to pseudomonic acid itself.

(b) Formulation C vs. Formulation D

The formulation containing mupirocin free acid plus hydrocortisone (Formulation D) was more unstable than that containing mupirocin free acid alone (Formulation C), indicating that hydrocortisone has a destabilising influence on the mupirocin in the formulation. The effect was discernible under all the conditions studied, especially at 37° C. after both 4 and 8 months. Again, in view of the poor stability after 8 months at 37°, the test was terminated.

(c) Formulation A vs. Formulation B

Since the tests on Formulations C and D showed that hydrocortisone has a destabilising influence on mupirocin, it would have been expected that the presence of hydrocortisone would have a similar adverse effect on the stability of calcium mupirocin. Therefore it would have been expected that Formulation B would be less stable than Formulation A in the same way that Formulation D is less stable than Formulation C. However, the results unexpectedly show there to be no adverse effect: the Table shows that Formulation B has the same excellent stability under all conditions as does Formulation A in which hydrocortisone is absent, even after 24 months at 37.C. This surprising finding is of great commercial importance in view of the degree of thermal stability demanded for pharmaceutical preparations, especially in tropical markets, and in view of the fact that a 2-year shelf life is regarded as the minimum commercial viable.

We claim:

1. A pharmaceutical composition for topical application to humans or domestic mammals comprising the hydrated crystalline calcium salt of mupirocin, and a corticosteroid intimately mixed therewith.

2. A composition according to claim 1, which comprises 0.01 to 50% of the hydrated crystalline calcium salt of mupirocin.

3. A composition according to claim 1, which comprises from 0.001 to 5% of the corticosteroid.

4. A composition according to claim 1, which comprises from 1 to 3% of the hydrated crystalline calcium salt of mupirocin and from 0.1 to 2% of the corticosteroid.

5. A composition according to claim 1, wherein the corticosteroid is hydrocortisone.

6. A composition according to claim 1 containing approximately 2% of mupirocin crystalline calcium salt dihydrate (calculated as mupirocin), and approximately 1% of hydrocortisone in an ointment base, the ointment base containing approximately 95% of white soft paraffin and approximately 5% of 'Softisan 649'.

* * * * *